(12) United States Patent
Ysebaert et al.

(10) Patent No.: US 10,363,253 B2
(45) Date of Patent: Jul. 30, 2019

(54) COMBINATION PRODUCTS FOR THE TREATMENT OF RSV

(71) Applicant: Janssen Sciences Ireland Unlimited Company, County Cork (IE)

(72) Inventors: Nina Ysebaert, Beerse (BE); Nele Isa E. Goeyvaerts, Beerse (BE); Dirk André E. Roymans, Beerse (BE); Anil Koul, Beerse (BE)

(73) Assignee: Janssen Sciences Ireland Unlimited Company, Ringaskiddy, Co Cork (IE)

( * ) Notice: Subject to any disclaimer, the term of this patent is extended or adjusted under 35 U.S.C. 154(b) by 0 days.

(21) Appl. No.: 16/075,103

(22) PCT Filed: Feb. 2, 2017

(86) PCT No.: PCT/EP2017/052201
§ 371 (c)(1),
(2) Date: Aug. 2, 2018

(87) PCT Pub. No.: WO2017/134133
PCT Pub. Date: Aug. 10, 2017

(65) Prior Publication Data
US 2019/0054084 A1    Feb. 21, 2019

(30) Foreign Application Priority Data

Feb. 3, 2016  (EP) .................................. 16154035

(51) Int. Cl.

| | |
|---|---|
| *A61K 31/496* | (2006.01) |
| *A61K 31/7056* | (2006.01) |
| *A61K 31/519* | (2006.01) |
| *A61K 31/41* | (2006.01) |
| *A61K 39/42* | (2006.01) |
| *A61K 31/55* | (2006.01) |
| *A61K 31/4745* | (2006.01) |
| *A61P 31/14* | (2006.01) |
| *A61K 31/4184* | (2006.01) |
| *A61K 31/437* | (2006.01) |
| *A61K 31/52* | (2006.01) |
| *A61K 31/53* | (2006.01) |
| *A61K 31/5377* | (2006.01) |
| *A61K 31/5513* | (2006.01) |
| *A61K 31/70* | (2006.01) |
| *C07K 16/10* | (2006.01) |
| *A61K 39/395* | (2006.01) |
| *A61K 39/00* | (2006.01) |

(52) U.S. Cl.
CPC ............ *A61K 31/496* (2013.01); *A61K 31/41* (2013.01); *A61K 31/4184* (2013.01); *A61K 31/437* (2013.01); *A61K 31/4745* (2013.01); *A61K 31/519* (2013.01); *A61K 31/52* (2013.01); *A61K 31/53* (2013.01); *A61K 31/5377* (2013.01); *A61K 31/55* (2013.01); *A61K 31/5513* (2013.01); *A61K 31/70* (2013.01); *A61K 31/7056* (2013.01); *A61K 39/42* (2013.01); *A61P 31/14* (2018.01); *C07K 16/10* (2013.01); *C07K 16/1027* (2013.01); *A61K 39/395* (2013.01); *A61K 2039/505* (2013.01)

(58) Field of Classification Search
None
See application file for complete search history.

(56) References Cited

U.S. PATENT DOCUMENTS 8,921,560 B2 * 12/2014 Cooymans ........... C07D 403/06
                                                     546/118

FOREIGN PATENT DOCUMENTS

| WO | 2012080447 | 6/2012 |
| WO | 2014174018 A1 | 10/2014 |
| WO | 2016055791 A1 | 4/2016 |

OTHER PUBLICATIONS

Mackman et al. J of Medi. Chem., (2015), 58, p. 1630-1643.*
(Continued)

*Primary Examiner* — Yong L Chu

(57) ABSTRACT

The present invention is directed to the combination of the RSV inhibiting Compound A, i.e. 3-({5-chloro-1-[3-(methylsulfonyl)propyl]-1H-indol-2-yl}methyl)-1-(2,2,2-trifluoroethyl) 1,3-dihydro-2H-imidazo[4,5-c]pyridin-2-one, and one or more RSV inhibiting Compound B selected from from ribavirin, GS-5806, MDT-637, BTA-9881, BMS-433771, YM-543403, A-60444, TMC-353121, RFI-641, CL-387626, MBX-300, AZ-27, MEDI8897, CR9501, palivizumab, 3-({5-chloro-1-[3-(methylsulfonyl)propyl]-1H-benzimidazol-2-yl}methyl)-1 cyclopropyl-1,3-dihydro-2H-imidazo[4,5-c]pyridin-2-one, 3-[[7-chloro-3-(2 ethylsulfonylethyl)imidazo[1,2-a]pyridin-2-yl]methyl]-1-cyclopropyl-imidazo[4,5-c]pyridin-2 one, N-(2-fluoro-6-methylphenyl)-6-(4-(5-methyl-2-(7-oxa-2-azaspiro[3.5]nonan-2 yl)nicotinamido)benzoyl)-5,6-dihydro-4H-benzo[b]thieno[2,3-d]azepine-2-carboxamide, and 4-amino-8-[3-[[2-(3,4-dimethoxyphenyl)ethyl]amino]propyl]-6,6-dimethyl-2-(4-methyl 3-nitrophenyl)-3H-imidazo[4,5-h]isoquinoline-7,9(6H,8H)-dione, for treating or ameliorating RSV infection. The invention further relates to the combination product of Compound A and one or more Compound B, a pharmaceutical product comprising Compound A and one or more Compound B, the use of the combination of Compound A and one or more of Compound B—or the pharmaceutical product comprising Compound A and one or more Compound B—for the treatment of RSV infection, and a method of treating or ameliorating RSV infection in a subject in need thereof comprising administering the combination of Compound A and one or more Compound B in an effective amount to said subject.

14 Claims, No Drawings

(56) References Cited

OTHER PUBLICATIONS

Online Registry via STN Apr. 1, 1980, RN 197365-88-1.
Online registry via STN Jan. 1, 1998, RN 199601-01-9.
Online Registry via STN Jan. 1, 2006, RN 188039-54-5.
Online Registry Via STN, Mar. 1, 1980, RN 197366-24-8.
International Search Report and Written Opinion for Corresponding Application No. PCT/EP2017/052201, dated Jul. 5, 2017.
Devincenzo et al., "Oral GS-5806 Activity in a Respiratory Syncytial Virus Challenge Study", New England Journal of Medicine, vol. 371 (8) pp. 711-722 (Aug. 21, 2014).
Gosh, et al., "IDWeek 2015. San Diego, California, USA—Oct. 7-11, 2015.", Drugs of the Future, vol. 40 (11);pp. 765 (Jan. 1, 2015).
Hallack, et al., "Glycosaminoglycan Sulfation Requirements for Respiratory Syncytial Virus Infection", Journal of Virology, vol. 74(22):pp. 10508-10513 (Nov. 2000).
Hu, et al., "Treatment of respiratory syncytial virus with palivizumab: a systematic review", World Journal of Pediatrics, vol. 6(4): pp. 296-300 (Nov. 1, 2010).
Krilov, et al., "Palivizumab in the prevention of respiratory syncytial virus disease", Expert Opinion on Biological Therapy, vol. 2 (7): pp. 763-769 (Oct. 1, 2002).
Mejias, et al, "New options in the treatment of respiratory syncytial virus disease", Journal of Infection, vol. 71: pp. 582 (Apr. 25, 2015).
Perron, et al, "GS-5806 Inhitts a Broad Range of Respiratory Syncytial Virus Clinical Isolated by Blocking the Virus-Cell Fusion Process", Antimicrobial Agents and Chemotherapy,vol. 60 (3) :pp. 1264-1273 (Dec. 14, 2015).
Whimbey, et al, "Combination therapy with aerosolized ribavirin and intravenous immunoglobulin for respiratory syncytial virus in adult bone marrow transplant recipients", Bone Marrow Transplantation, vol. 16(3): pp. 393-399 (Sep. 1, 1995).
Wyde, et al., "Comparison of the inhibition of human metapneumovirus and respiratory syncytial virus by ribavirin and immune serum globulin in vitro", Antiviral Research, vol. 60 (1): pp. 51-59 (Sep. 1, 2003).

\* cited by examiner

COMBINATION PRODUCTS FOR THE TREATMENT OF RSV

CROSS-REFERENCE TO RELATED APPLICATIONS

This application is a national phase entry of International Application No. PCT/EP2017/052201, filed on Feb. 2, 2017, which claims priority to EP Patent Application No. 16154035.6, filed on Feb. 3, 2016, each of which are incorporated herein in its entirety.

The present invention is directed to the combination of the RSV inhibiting Compound A, i.e. 3-({5-chloro-1-[3-(methylsulfonyl)propyl]-1H-indol-2-yl}methyl)-1-(2,2,2-trifluoroethyl)-1,3-dihydro-2H-imidazo[4,5-c]pyridin-2-one, and one or more RSV inhibiting Compound B selected from ribavirin, GS-5806, MDT-637, BTA-9881, BMS-433771, YM-543403, A-60444, TMC-353121, RFI-641, CL-387626, MBX-300, AZ-27, MED18897, CR9501, palivizumab, 3-({5-chloro-1-[3-(methylsulfonyl)propyl]-1H-benzimidazol-2-yl}methyl)-1-cyclopropyl-1,3-dihydro-2H-imidazo[4,5-c]pyridin-2-one, 3-[[7-chloro-3-(2-ethylsulfonylethyl)imidazo[1,2-a]pyridin-2-yl]methyl]-1-cyclopropyl-imidazo[4,5-c]pyridin-2-one, N-(2-fluoro-6-methylphenyl)-6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxamide, and 4-amino-8-[3-[[2-(3,4-dimethoxyphenyl)ethyl]amino]propyl]-6,6-dimethyl-2-(4-methyl-3-nitrophenyl)-3H-imidazo[4,5-h]isoquinoline-7,9(6H,8H)-dione for treating or ameliorating RSV infection. The invention further relates to the combination product of Compound A and one or more Compound B, a pharmaceutical product comprising Compound A and one or more Compound B, the use of the combination of Compound A and one or more of Compound B—or the pharmaceutical product comprising Compound A and one or more Compound B—for the treatment of RSV infection, and a method of treating or ameliorating RSV infection in a subject in need thereof comprising administering the combination of Compound A and one or more Compound B in an effective amount to said subject.

Human RSV or Respiratory Syncytial Virus is a large RNA virus—member of the family of Pneumoviridae, genus Orthopneumovirus—together with bovine RSV virus. Human RSV is responsible for a spectrum of respiratory tract diseases in people of all ages throughout the world. It is the major cause of lower respiratory tract illness during infancy and childhood. Over half of all infants encounter RSV in their first year of life, and almost all within their first two years. The infection in young children can cause lung damage that persists for years and may contribute to chronic lung disease in later life (chronic wheezing, asthma). Older children and adults often suffer from a (bad) common cold upon RSV infection. In old age, susceptibility again increases, and RSV has been implicated in a number of outbreaks of pneumonia in the aged resulting in significant mortality.

Today only three drugs have been approved for use against RSV infection. A first one is ribavirin, a nucleoside analogue that provides an aerosol treatment for serious RSV infection in hospitalized children. The other two drugs, RespiGam® (RSV-IG) and Synagis® (palivizumab), polyclonal and monoclonal antibody immunostimulants, are intended to be used in a preventive way. Both are very expensive, and require parenteral administration. A number of compounds are in clinical development for the treatment of RSV infection. One of those compounds is 3-({5-chloro-1-[3-(methylsulfonyl)-propyl]-1H-indol-2-yl}methyl)-1-(2,2,2-trifluoroethyl)-1,3-dihydro-2H-imidazo[4,5-c]pyridin-2-one disclosed in WO-2012/080447 as compound P55.

It has now been found that the combination of 3-({5-chloro-1-[3-(methylsulfonyl)-propyl]-1H-indol-2-yl}methyl)-1-(2,2,2-trifluoroethyl)-1,3-dihydro-2H-imidazo[4,5-c]pyridin-2-one (hereinafter referred to as Compound A) and one or more Compound B, wherein Compound B has RSV replication inhibiting properties, provides an improved therapy in the treatment of RSV infection.

Some embodiments disclosed herein relate to the combination of Compound A and one or more Compound B and the use of this combination for treating or ameliorating RSV infection in a subject in need thereof.

Other embodiments relate to a pharmaceutical product comprising the combination of Compound A and one or more Compound B and the use of said pharmaceutical product for treating or ameliorating RSV infection.

Still other embodiments relate to a method of treating or ameliorating RSV infection in a subject in need thereof comprising administering the combination of Compound A and one or more Compound B in an effective amount to said subject.

Compound A is 3-({5-chloro-1-[3-(methylsulfonyl)propyl]-1H-indol-2-yl}methyl)-1-(2,2,2-trifluoroethyl)-1,3-dihydro-2H-imidazo[4,5-c]pyridin-2-one disclosed in WO-2012/080447 as compound P55 having the following structure:

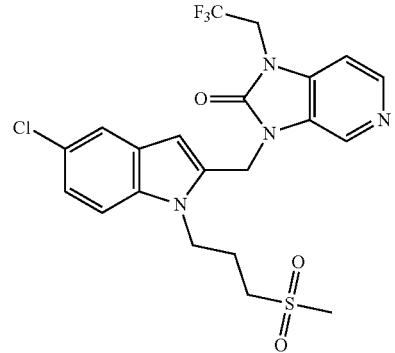 [SMILES: CS(=O)(=O)CCCn1c(Cn2c(=O)n(CC(F)(F)F)c3ccncc32)cc2cc(Cl)ccc21]

The one or more RSV inhibiting Compound B is individually selected from ribavirin, GS-5806, MDT-637, BTA-9881, BMS-433771, YM-543403, A-60444, TMC-353121, RFI-641, CL-387626, MBX-300, AZ-27, MED18897, CR9501, palivizumab, 3-({5-chloro-1-[3-(methylsulfonyl)propyl]-1H-benzimidazol-2-yl}methyl)-1-cyclopropyl-1,3-dihydro-2H-imidazo[4,5-c]pyridin-2-one, 3-[[7-chloro-3-(2-ethylsulfonylethyl)imidazo[1,2-a]pyridin-2-yl]methyl]-1-cyclopropyl-imidazo[4,5-c]pyridin-2-one, N-(2-fluoro-6-methylphenyl)-6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxamide, and 4-amino-8-[3-[[2-(3,4-dimethoxyphenyl)ethyl]amino]propyl]-6,6-dimethyl-2-(4-methyl-3-nitrophenyl)-3H-imidazo[4,5-h]isoquinoline-7,9(6H,8H)-dione.

| Structure or CAS registry of Compounds B | Alias | Scientific name |
|---|---|---|
| | ribavirin | 1-β-D-ribofuranosyl-1H-1,2,4-triazole-3-carboxamide |
| | GS-5806 | N-(2-((S)-2-(5-((S)-3-aminopyrrolidin-1-yl)-6-methylpyrazolo[1,5-a]pyrimidin-2-yl)piperidine-1-carbonyl)-4-chlorophenyl)methane-sulfonamide |
| | MDT-637 (VP-14637) | 2,2'-[(4-hydroxyphenyl)-methylene]bis[4-[[(5-methyl-1H-tetrazol-1-yl)imino] methyl]-phenol |
| | BTA-9881 | (9bS)-9b-(4-chlorophenyl)-1-(pyridin-3-ylcarbonyl)-1,2,3,9b-tetrahydro-5H-imidazo[10,20:1,2]pyrrolo[3,4-c]pyridin-5-one |
| | BMS-433771 | 1-cyclopropyl-3-[[1-(4-hydroxybutyl)-1H-benzimidazol-2-yl]methyl]-1,3-dihydroimidazo[4,5-c]pyridin-2-one |

-continued

| Structure or CAS registry of Compounds B | Alias | Scientific name |
|---|---|---|
| [structure] | YM-53403 | 6-[4-[([1,1'-biphenyl]-2-yl-carbonyl)amino]benzoyl]-N-cyclopropyl-5,6-dihydro-4H-thieno[3,2-d][1]benzazepine-2-carboxamide |
| [structure] | A-60444 (=RSV604) | (S)-1-(2-fluorophenyl)-3-(2-oxo-5-phenyl-2,3-dihydro-1H-benzo[e][1,4]diazepin-3-yl) urea |
| [structure] | TMC-353121 | 2-[[6-[[[2-(3-hydroxypropyl)-5-methylphenyl]amino]methyl]-2-[[3-(morpholin-4-yl)-propyl]amino]benzimidazol-1-yl] methyl]-6-methylpyridin-3-ol |
| CAS registry no. 197366-24-8 | RFI-641 | [1,1'-biphenyl]-2,2'-disulfonic acid, 4,4'-bis[[4,6-bis[[3-[[bis (2-amino-2-oxoethyl)-amino]sulfonyl]phenyl]amino]-1,3,5-triazin-2-yl]amino]-disodium salt |
| CAS registry no. 197365-88-1 | CL-387626 | [1,1'-biphenyl]-2,2'-disulfonic acid, 4,4'-bis[[4,6-bis[[3-[[bis (3-amino-3-oxopropyl)-amino] sulfonyl]phenyl]amino]-1,3,5-triazin-2-yl]amino]-disodium salt |
| CAS registry no. 199601-01-9 | MBX-300 or NMSO3 | α-neuraminic acid, N-acetyl-2-O-[3-(docosyloxy)-2-[(docosyloxy)methyl]-2-methylpropyl]-,4,7,8,9-tetrakis(hydrogen sulfate) pentasodium salt |

-continued

| Structure or CAS registry of Compounds B | Alias | Scientific name |
|---|---|---|
| | AZ-27 | N-cyclopropyl-5,6-dihydro-6-[4-[[[2-(2-oxa-7-azaspiro[3.5]non-7-yl)-3-pyridinyl]carbonyl]-amino]benzoyl]-4H-thieno[3,2-d][1]benzazepine-2-carboxamide |
| | | 3-({5-chloro-1-[3-(methylsulfonyl)propyl]-1H-benzimidazol-2-yl}methyl)-1-cyclopropyl-1,3-dihydro-2H-imidazo[4,5-c]pyridin-2-one |
| | | 3-[[7-chloro-3-(2-ethylsulfonylethyl)imidazo[1,2-a]-pyridin-2-yl]methyl]-1-cyclopropyl-imidazo[4,5-c]pyridin-2-one |
| monoclonal antibody | MEDI8897 | |
| monoclonal antibody | CR9501 | |
| monoclonal antibody CAS 188039-54-5 | palivizumab | |

| Structure or CAS registry of Compounds B | Alias | Scientific name |
|---|---|---|
| 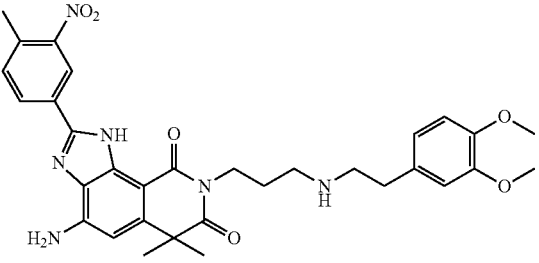 [SMILES: COc1ccc(CCNCCCN2C(=O)c3c(cc(N)c4nc(-c5ccc(C)c([N+](=O)[O-])c5)[nH]c34)C(C)(C)C2=O)cc1OC] | CAS 851658-10-1 | 4-amino-8-[3-[[2-(3,4-dimethoxyphenyl)ethyl]amino]propyl]-6,6-dimethyl-2-(4-methyl-3-nitrophenyl)-3H-imidazo[4,5-h]isoquinoline-7,9(6H,8H)-dione |
| 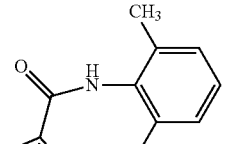 | pulmocide | N-(2-fluoro-6-methylphenyl)-6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxamide |

Whenever used hereinafter, the term Compound A, Compound B, one or more Compound B, Compounds B or similar term it is meant to include both the Compound A and/or Compound B in its free base form and the pharmaceutically acceptable salt forms thereof.

The Compound A or Compounds B may be used in pharmaceutically acceptable salt forms or in free (i.e. non-salt) form. Salt forms can be obtained by treating the free form with an acid or base. Of interest are the pharmaceutically acceptable acid and base addition salts, which are meant to comprise the therapeutically active non-toxic acid and base addition salt forms that the compounds are able to form. The pharmaceutically acceptable acid addition salts of the Compound A or Compounds B can conveniently be obtained by treating the free form with such appropriate acid. Appropriate acids comprise, for example, inorganic acids such as hydrohalic acids, such as hydrobromic acid, or in particular hydrochloric acid; or sulfuric, nitric, phosphoric and the like acids; or organic acids such as, for example, acetic, propanoic, hydroxyacetic, lactic, pyruvic, oxalic, malonic, succinic, maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. The Compound A or Compounds B may also be converted into the pharmaceutically acceptable metal or amine addition salt forms by treatment with appropriate organic or inorganic bases. Appropriate base salt forms comprise, for example, the ammonium salts, the alkali and earth alkaline metal salts, e.g. the lithium, sodium or potassium salts; or the magnesium or calcium salts; salts with organic bases, e.g. the benzathine, N-methyl-D-glucamine, hydrabamine salts, and salts with amino acids such as, for example, arginine, lysine, and the like. The term addition salt form is meant to also comprise any solvates that Compound A or Compounds B, as well as the salts thereof, may form. Such solvates are, for example, hydrates, alcoholates, e.g. ethanolates, and the like.

A first group of Compounds B is wherein Compound B is selected from ribavirin, GS-5806, MDT-637, A-60444, AZ-27, CR9501, palivizumab, N-(2-fluoro-6-methylphenyl)-6-(4-(5-methyl-2-(7-oxa-2-azaspiro[3,5]nonan-2-yl)nicotinamido)benzoyl)-5,6-dihydro-4H-benzo[b]thieno[2,3-d]azepine-2-carboxamide, and 4-amino-8-[3-[[2-(3,4-dimethoxyphenyl) ethyl]amino]propyl]-6,6-dimethyl-2-(4-methyl-3-nitrophenyl)-3H-imidazo[4,5-h]isoquinoline-7,9(6H,8H)-dione.

A second group of Compounds B is wherein Compound B is selected from the monoclonal antibody MED18897, CR9501, and palivizumab; in particular Compound B is palivizumab.

A third group of Compounds B is wherein Compound B is selected from ribavirin, GS-5806, MDT-637, A-60444 and AZ-27.

A fourth group of Compounds B is wherein Compound B is selected from N-(2-fluoro-6-methylphenyl)-6-(4-(5-methyl-2-(7-oxa-2-azaspiro[3.5]nonan-2-yl)nicotinamido)-benzoyl)-5,6-dihydro-4H-benzo[b]thieno[2,3-d]azepine-2-carboxamide, and 4-amino-8-[3-[[2-(3,4-dimethoxyphenyl)ethyl]amino]propyl]-6,6-dimethyl-2-(4-methyl-3-nitrophenyl)-3H-imidazo[4,5-h]isoquinoline-7,9(6H,8H)-dione.

In an embodiment the amount of Compound A and the amount of Compound B in the combinations according to the present invention is such that a synergistic antiviral effect against RSV is obtained.

The amounts of the Compound A in the combinations of the invention that are administered on a daily basis may vary from about 10 mg to about 2500 mg, about 50 mg to about 1000 mg, or from about 50 mg to about 500 mg.

The amounts of the one or more Compound B in the combinations of the invention that are administered on a daily basis may vary from about 10 mg to about 2500 mg, about 50 mg to about 1000 mg, or from about 50 mg to about 500 mg for the total amount of the one or more Compound B.

All amounts mentioned in this and the following paragraphs refer to the free form (i.e. non-salt form). The above values represent free-form equivalents, i.e. quantities as if the free form would be administered. If salts are administered the amounts need to be calculated in function of the molecular weight ratio between the salt and the free form.

The above mentioned daily doses are calculated for an average body weight of about 70 kg and should be recalculated in case of paediatric applications, or when used with patients with a substantially diverting body weight.

The dosages may be presented as one, two, three or four or more sub-doses administered at appropriate intervals throughout the day. The dosage used preferably corresponds to the daily amount of Compound A and one or more Compounds B mentioned above, or a sub-dose thereof, such as ½, ⅓, or ¼ thereof. A dosage form may contain the Compound A and one or more Compounds B, in an amount equal to the ranges or quantities mentioned in the previous paragraphs, either in separate formulations or in a combined formulation. Such combined formulation is preferred.

In the instance where Compound A and one or more Compounds B are to be administered once daily, this can be accomplished by administering a combined fixed dose combination containing Compound A and one or more Compounds B. Dosage forms that can be administered are described hereinafter, oral dosage forms, in particular oral solutions being preferred.

Active ingredients may be formulated in pharmaceutical compositions either separately or as a combined pharmaceutical composition. In the latter instance, there is provided a pharmaceutical composition comprising a therapeutically effective amount of Compound A, or a pharmaceutically acceptable salt thereof, and the one or more Compounds B, or a pharmaceutically acceptable salt thereof, and a pharmaceutically acceptable carrier. A therapeutically effective amount in this context is an amount sufficient to stabilize or to reduce RSV infection, in infected subjects. Therapeutically effective amounts may in particular correspond to the amounts mentioned above for administration on a daily base or of the subdoses thereof in ease of multiple daily administrations.

In a further aspect, this invention relates to a process of preparing a pharmaceutical composition as specified herein, which comprises intimately mixing a pharmaceutically acceptable carrier with a therapeutically effective amount of the Compound A, or a pharmaceutically acceptable salt thereof, and an effective amount of the one or more Compounds B, or a pharmaceutically acceptable salt thereof.

The combinations provided herein may also be formulated as a combined preparation for simultaneous or sequential use in RSV therapy. In such a case, the Compound A is formulated in a pharmaceutical composition containing other pharmaceutically acceptable excipients, and the one or more Compounds B is formulated separately in a pharmaceutical composition containing other pharmaceutically acceptable excipients. Conveniently, these separate pharmaceutical compositions can be part of a kit for simultaneous or sequential use.

The individual components of the combination of the present invention can be administered simultaneously or separately at different times during the course of therapy or concurrently in divided or single combination forms.

Therefore, the Compound A and one or more Compounds B, individually or combined, may be formulated into various pharmaceutical compositions suitable for administration purposes. In these, a therapeutically effective amount of each of the particular compounds A and B is combined with a pharmaceutically acceptable carrier, which carrier may take a wide variety of forms depending on the form of preparation desired for administration. Pharmaceutical compositions may be prepared as medicaments to be administered orally, parenterally (including subcutaneously, intramuscularly, and intravenously), rectally, bucally, or nasally. Suitable compositions for oral administration include powders, granulates, aggregates, tablets, compressed or coated pills, dragees, sachets, hard or gelatin capsules, syrups and suspensions. Suitable compositions for parenteral administration include aqueous or non-aqueous solutions or emulsions, while for rectal administration suitable compositions for administration include suppositories with a hydrophilic or hydrophobic vehicle. For nasal delivery there can be used suitable aerosol delivery systems.

For example, in preparing the compositions for oral administration, any of the usual pharmaceutical media may be employed such as, for example, water, glycols, oils, alcohols and the like in the case of oral liquid compositions such as suspensions, syrups, elixirs, emulsions and solutions; or solid carriers such as starches, sugars, kaolin, lubricants, binders, disintegrating agents and the like in the case of solid compositions. For parenteral compositions, the carrier will usually comprise sterile water, at least in large part, though other ingredients, such as solubilizers, emulsifiers or further auxiliaries may be added thereto. Injectable solutions may be prepared in which the carrier comprises saline solution, glucose solution or a mixture of both. Injectable suspensions may also be prepared in which case appropriate liquid carriers, suspending agents and the like may be employed. Also included are solid form preparations intended to be converted, shortly before use, to liquid form preparations such as powders for reconstitution.

The pharmaceutical compositions may be conveniently presented in unit dosage form for ease of administration and uniformity of dosage. Examples include tablets (including scored or coated tablets), capsules, pills, suppositories, powder packets, wafers, injectable solutions or suspensions and the like, and segregated multiples thereof.

The combination of Compound A and one or more Compounds B, as specified herein, is useful in the treatment of warm-blooded animals, in particular humans, infected with RSV.

The present invention also relates to a method for treating or ameliorating RSV infection in a subject in need thereof comprising administering the combination of Compound A and one or more Compound B, or a pharmaceutically acceptable salt of any of the foregoing, in a therapeutically effective amount to said subject. The amount of Compound A can range from 5 mg/kg to 50 mg/kg and the amount of Compound B can range from 5 mg/kg to 50 mg/kg.

In an embodiment the present invention further relates to a method for treating or ameliorating RSV infection in a subject in need thereof comprising administering the combination of Compound A and one or more Compound B, or a pharmaceutically acceptable salt of any of the foregoing, wherein the amount of Compound A and the amount of Compound is such that a synergistic antiviral effect against RSV is obtained.

Other embodiments relate to a method for treating or ameliorating a RSV infection comprising contacting a cell infected with the RSV virus with an effective amount of a combination of Compound A and one or more of Compound B, or a pharmaceutically acceptable salt of any of the foregoing.

As used herein, the terms "treat," "treating," "treatment," "therapeutic," and "therapy" do not necessarily mean total cure or abolition of the disease or condition. Any reduction of viral load or alleviation of any undesired signs or symptoms of a disease or condition, to any extent can be considered treatment and/or therapy.

The terms "therapeutically effective amount" and "effective amount" are used to indicate an amount of an active compound, or pharmaceutical agent, that elicits the biological or medicinal response indicated. For example, a therapeutically effective amount of compound can be the amount needed to prevent, alleviate or ameliorate symptoms of disease, reduce viral load, or prolong the survival of the subject being treated. This response may occur in a tissue, system, animal or human and includes reduction of viral load, alleviation of the signs or symptoms of the disease being treated. Determination of an effective amount is well within the capability of those skilled in the art, in view of the disclosure provided herein. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

Various indicators for determining the effectiveness of a method for treating a respiratory syncytical virus (RSV) infection are known to those skilled in the art. Example of suitable indicators include, but are not limited to, a reduction in viral load, a reduction in viral replication, a reduction in time to seroconversion (virus undetectable in patient serum), a reduction of morbidity or mortality in clinical outcomes, and/or other indicator of disease response.

In some embodiments, a combination of Compound A and one or more of Compound B, or a pharmaceutical acceptable salt of the foregoing, can reduce viral titers to undetectable levels, for example, less than 1.7 $\log_{10}$ plaque forming units equivalents (PFUe)/mL, or less than 0.3 $\log_{10}$ plaque forming units equivalents (PFUe)/mL. In some embodiments, a combination of compounds described herein can reduce the viral load compared to the viral load before administration of the combination (for example, 60 hours after receiving the initial dosage of the combination). In some embodiments, a combination of compounds described herein can reduce the viral load to lower than 1.7 $\log_{10}$ (PFUe)/mL, or lower than 0.3 $\log_{10}$ (PFUe)/mL. In some embodiments, a combination of compounds described herein can achieve a reduction in viral titer in the serum of the subject in the range of about 1.5-log to about a 2.5-log reduction, about a 3-log to about a 4-log reduction, or a greater than about 5-log reduction compared to the viral load before administration of the combination. For example, the viral load is measure before administration of the combination, and several hours after receiving the initial dosage of the combination (for example, 60 hours after receiving the initial dosage of the combination).

In some embodiments, a combination of Compound A and one or more of Compound B, or a pharmaceutical acceptable salt of the foregoing, can result in at least a 1, 2, 3, 4, 5, 10, 15, 20, 25, 50, 75, 100-fold or more reduction in the replication of RSV relative to pre-treatment levels in a subject, as determined several hours after receiving the initial dosage of the combination (for example, 60 hours after receiving the initial dosage of the combination). In some embodiments, a combination as described herein can result in a reduction of the replication of RSV relative to pre-treatment levels in the range of about 2 to about 5 fold, about 10 to about 20 fold, about 15 to about 40 fold, or about 50 to about 100 fold. In some embodiments, a combination as described herein can result in a reduction of RSV replication in the range of 1 to 1.5 log, 1.5 log to 2 log, 2 log to 2.5 log, 2.5 to 3 log, 3 log to 3.5 log or 3.5 to 4 log more reduction of RSV replication compared to the reduction of RSV reduction achieved by the use of one anti-RSV agent administered as monotherapy, or may achieve the same reduction in a shorter period of time.

After a period of time, infectious agents can develop resistance to one or more therapeutic agents. The term "resistance" as used herein refers to a viral strain displaying a delayed, lessened and/or null response to a therapeutic agent(s). For example, after treatment with an antiviral agent, the viral load of a subject infected with a resistant virus may be reduced to a lesser degree compared to the amount in viral load reduction exhibited by a subject infected with a nonresistant strain. In some embodiments, a combination of Compound A and one or more of Compound B, or a pharmaceutical acceptable salt of the foregoing, can be administered to a subject infected with RSV that is resistant to one or more different anti-RSV agents (for example, ribavirin). In some embodiments, development of resistant RSV strains can be delayed when subjects are treated with combination of compounds described herein compared to the development of RSV strains resistant to other anti-RSV agents administered as monotherapy.

In some embodiments, a combination of Compound A and one or more of Compound B, or a pharmaceutical acceptable salt of the foregoing, can decrease the percentage of subjects that experience complications from a RSV viral infection compared to the percentage of subjects that experience complication being treated with one anti-RSV agent. For example, the percentage of subjects being treated with a combination of compounds described herein that experience complications can be 5%, 10%, 25%, 40%, 50%, 60%, 70%, 80% and 90% less compared to subjects being treated with only one anti-RSV agent administered as monotherapy.

A potential advantage of utilizing a combination of Compound A and one or more of Compound B, or a pharmaceutical acceptable salt of the foregoing, may be a reduction in the required amount(s) of Compound A, or a pharmaceutically acceptable salt thereof, and/or one or more of Compound B, or a pharmaceutically acceptable salt thereof, that is effective in treating RSV infection, as compared to the amount required to achieve same therapeutic result when one or more of Compound (B), or a pharmaceutically acceptable salt thereof, and/or Compound A, or a pharmaceutically acceptable salt thereof. For example, the amount of Compound A, or a pharmaceutically acceptable salt thereof, and/or one or more of Compound B, or a pharmaceutically acceptable salt thereof, can be less compared to the amount of the aforementioned compounds needed to achieve the same viral load reduction when administered as a monotherapy. Another potential advantage of utilizing a combination described herein is that the use of two or more compounds having different mechanism of actions can create a higher barrier to the development of resistant viral strains compared to the barrier when a compound is administered as monotherapy. Additional advantages of utilizing a combination described herein may include little to no cross resistance between the compounds of the combination; different routes for elimination of the compounds of the combination; little to no overlapping toxicities between the compounds of the combination; little to no significant effects on cytochrome P450; and/or little to no pharmacokinetic interactions between the compounds of the combination.

EXAMPLES

The following examples are intended to illustrate the present invention and not to limit it thereto.

Example 1: RSV Assay

Black 384-well clear-bottom microtiter plates (Corning, Amsterdam, The Netherlands) were filled via acoustic drop ejection using the echo liquid handler (Labcyte, Sunnyvale, Calif.). 200 nL of compound stock solutions (100% DMSO) were transferred to the assay plates. Compound (A), or a pharmaceutically acceptable salt thereof, was serially diluted (1:3) to 12 distinct concentrations "horizontally" in a 384-well plate, and Compound (B), or a pharmaceutically acceptable salt thereof, was serially diluted (1:3) to 12 distinct concentrations "vertically" in 384-well plate. Space was also allotted for titrations of each of the compounds alone to be used as reference controls. The assay was initiated by adding 10 µL of culture medium to each well (RPMI medium without phenol red, 10% FBS-heat inactivated, 0.04% gentamycin (50 mg/mL). All addition steps are done by using a multidrop dispenser (Thermo Scientific, Erembodegem, Belgium). Next, rgRSV224 virus (MOI=1) diluted in culture medium was added to the plates. rgRSV224 virus is an engineered virus that includes an additional GFP gene (Hallak L K, Spillmann D, Collins P L, Peeples M E. Glycosaminoglycan sulfation requirements for respiratory syncytial virus infection; Journal of virology (2000), 74(22), 10508-13) and was in-licensed from the NIH (Bethesda, Md., USA). Finally, 20 µL of a HeLa cell suspension (3,000 cells/well) were plated. Medium, virus- and mock-infected controls were included in each test. The wells contain 0.05% DMSO per volume. Cells were incubated at 37° C. in a 5% CO2 atmosphere. Three days post-virus exposure, viral replication was quantified by measuring GFP expression in the cells by an in house developed MSM laser microscope (Tibotec, Beerse, Belgium). The $EC_{50}$ was defined as the 50% inhibitory concentration for GFP expression.

Cell Viability Assay

In parallel, compounds were incubated for three days in a set of white 384-well microtiter plates (Corning) and the cytotoxicity of compounds in HeLa cells was determined by measuring the ATP content of the cells using the ATPlite kit (Perkin Elmer, Zaventem, Belgium) according to the manufacturer's instructions. The $CC_{50}$ was defined as the 50% concentration for cytotoxicity.

Data Analysis

Each experiment was performed at N=3 for both anti-RSV activity and cell viability. Mean percent inhibition of the replicon values from the 3 experiments was generated and for anti-RSV activity, a Combination Index (CI) is calculated by the Program CalCuSyn a Biosoft software (Biosoft, UK): $CI=[(D)1/(Dx)1]+[(D)2/(Dx)2]$. A combination is defined as: CI<1: synergy; CI>1: antagonism; CI=1: additive. A more detailed range of CI is provided in the table below.

| Range of CI | Description | Symbols |
|---|---|---|
| <0.1 | Very strong synergism | ++++++ |
| 0.1-0.3 | Strong synergism | ++++ |
| 0.3-0.7 | Synergism | +++ |
| 0.7-0.85 | Moderate synergism | ++ |
| 0.85-0.90 | Slight synergism | + |
| 0.90-1.10 | Nearly additive | +/− |
| 1.10-1.20 | Slight antagonism | − |
| 1.20-1.45 | Moderate antagonism | −− |
| 1.45-3.3 | Antagonism | −−− |
| 3.3-10 | Strong antagonism | −−−− |
| >10 | Very strong antagonism | −−−−− |

Example 2: Combination Studies—RSV with *Renilla* Reporter

RSV expressing *Renilla* luciferase (A2-RL-line19F) was generated by Dr. Martin Moore of Emory University, Atlanta, Ga., USA. The in vitro viral kinetics of A2-RL-line19F is similar to that of wild type RSV. Host cell HEp-2 was purchased from ATCC (Cat. #CCL-23) and cells were cultured in DMEM/Ham's F-12 50/50 lx containing L-glutamine and 15 mM HEPES (Mediatech, Cat. #10-092-CM). The medium was further supplemented with 5% (v/v) FBS (Mediatech, Cat. #35-010-CV) and 1% (v/v) penicillin/streptomycin (Mediatech, Cat. #30-002-CI). HEp-2 cells were maintained at 37° C. in a humidified 5% $CO_2$ atmosphere.

Drug Treatment and Viral Dosing

To determine the effect of a combination of compounds, the following procedure was followed. On the first day, 20,000 HEp-2 cells were plated per well in a 96-well plate. On the following day, test articles were solubilized in 100% DMSO to 200× the desired final testing concentration. Subsequently, Compound (A), or a pharmaceutically acceptable salt thereof, was serially diluted (1:3) to 9 distinct concentrations "horizontally" in a 96-well plate, and Compound (B), or a pharmaceutically acceptable salt thereof, was serially diluted (1:3) to 7 distinct concentrations "vertically" in 96-well plate. The serially diluted 200× test articles were then diluted 1:10 into cell culture media to generate 20× test articles. A 5 μL aliquot of the 20× test articles was added in a checkerboard fashion to the cells with 90 μL existing media. Space was also allotted for titrations of each of the compounds alone to be used as reference controls. After 12 hour pre-incubation of test articles, A2-RL-line19F at an MOI of 0.5 was added to the plate and further incubated for 2 days at 37° C. in a 5% $CO_2$.

Determination of Anti-RSV Activity

The *Renilla* Luciferase Assay System (Promega, Cat. # E2820) was used to measure anti-RSV replicon activity. Assay plates were set up as stated above. Luminescence was recorded using a Perkin Elmer multilabel counter Victor3V.

Cell Viability Assay

Promega CellTiter-Glo Luminescent Cell Viability Assay, Cat. #G7572) was used to measure cell viability. The Cell-Titer-Glo® Luminescent Cell Viability Assay is a homogeneous method to determine the number of viable cells in culture based on quantitation of the adenosine triphosphate (ATP) present, which signals the presence of metabolically active cells. Assay plates were set up in the same format the anti-RSV assay, except that no virus was added to the cell viability assay. A 100-μL aliquot of CellTiter-Glo reagent was added to each well and incubated at room temperature for 8 minutes. Luminescence was recorded using a Perkin Elmer multilabel counter Victor3V.

Data Analysis

Each experiment was performed at N=5 for both anti-RSV activity and cell viability. Mean percent inhibition of the replicon values from the 5 experiments was generated and for anti-RSV activity, it was analyzed using two drug interaction analysis models, Isobologram Analysis and/or Prichard's Model.

Isobologram Analysis

The effects of drug-drug combinations were evaluated by the Loewe additivity model in which the experimental data were analyzed using CalcuSyn (Biosoft, Ferguson, Mo.), a computer program based on the method of Chou and Talalay. The combination index (CI) value and the isobologram for each experimental combination were calculated. CI values of <1, 1, and >1 indicate synergy, additive effect, and antagonism, respectively. Under the synergy category, CI<0.1 is considered very strong synergism; CI 0.1-0.3 strong synergism; CI 0.3-0.7 synergism and CI 0.7-0.85 moderate synergism. The isobologram analysis, which graphically represents additive, synergistic, and antagonistic drug effects, was also used to model the interaction of antiviral activities. In this representation, an effective concentration (EC) value of one drug is plotted on one axis and corresponding EC value of a second drug is plotted on the second axis; the line connecting these two points represents the amount of each drug in a combination that would be required to reach the equivalent EC value, given that their effects are additive.

Prichard's Model (Mac Synergy II)

MacSynergy II software was kindly provided by Dr. M. Prichard (University of Michigan). This program allows the three-dimensional examination of drug interactions of all data points generated from the checkerboard combination of two inhibitors with Bliss-Independence model. Confidence bounds are determined from replicate data. If the 95% confidence limits (CL) do not overlap the theoretic additive surface, then the interaction between the two drugs differs significantly from additive. The volumes of synergy or antagonism can be determined and graphically depicted in three dimensions and represent the relative quantity of synergism or antagonism per change in the two drug concentrations. Synergy and antagonism volumes are based on the Bliss independence model, which assumes that both compounds act independently on different targets. A set of predicted fractional responses faAB under the Bliss independence model is calculated as faAB=faA+faB−faA*faB with faA and faB representing the fraction of possible responses, e.g. % inhibition, of compounds A and B at amounts dA and dB, respectively, and describes the % inhibition of a combination of compounds A and B at amount (dA+dB). If faAB>faA+faB−faA*faB then we have Bliss synergy; if faAB<faA+faB−faA*faB then we have Bliss antagonism. The 95% synergy/antagonism volumes are the summation of the differences between the observed inhibition and the 95% confidence limit on the prediction of faAB under the Bliss independence model. Table 1 shows the volumes and corresponding volume descriptions for the results of the Bliss Independence Analysis. Mac Synergy II was used for data analysis.

TABLE 1

| MacSynergy II volume descriptions | |
|---|---|
| Volume (μM² %) | volume description |
| <25 | additive |
| 25-50 | minor synergism |
| 50-100 | significant synergism |
| >100 | strong synergism |

Example 3: RSV Assay Combination Experiments

To evaluate their combined antiviral effect against RSV, in vitro combination studies were performed with JNJ-53718678 ("compound A") and various compounds with different mechanisms-of-action ("compound B"). In short, 9 concentrations of Compound A were combined with 6 or 7 concentrations of a certain compound B. HeLa cells were infected with rgRSV224, an engineered RSV strain that encodes for eGFP (Hallak L K, Spillmann D, Collins P L, Peeples M E. Glycosaminoglycan sulfation requirements for respiratory syncytial virus infection; Journal of Virology (2000), 74(22), 10508-13), in the presence of various concentrations of compound A and compound B individually or in combination.

Compound stock solutions were 5 mM in 100% DMSO, with following exceptions: ribavirin, 20 mM; A 60444, 10 mM; CR9501, 141 μM in PBS; palivizumab, 156 μM in PBS; MDT 637, 100 μM in methanol. First, the compounds were serially diluted in 3-fold dilution series in DMSO; CR9501 and palivizumab were serially diluted in cell culture medium, and MDT 637 in methanol. The concentration series were diluted 100-fold in cell culture medium to achieve a combination matrix. 10 μL of these compound solutions were transferred to black 384-well clear-bottom tissue-culture treated plates. Next, 10 μL of a 150000 cells per mL HeLa cell suspension was added to achieve 3000 cells per well. Finally, 10 μL of diluted virus stock was added to achieve an MOI of 1. The final DMSO concentration of all wells was 0.5% DMSO, except for the MDT 637 experiment where it was 0.25% DMSO+0.25% methanol. Each combination of compound concentrations was tested in 4 replicates on 3 separate plates, resulting in a total of 12 replicates. The plates were incubated for 3 days at 37° C. in a humidified atmosphere at 5% CO2. The GFP signal was measured with PerkinElmer EnVision apparatus using a 405 nm filter.

For the statistical analysis, the observed GFP signal was normalized using the virus controls (VC) and cell controls (CC) on the corresponding plate: response=(GFP−CC)/(VC−CC), where CC was computed as the median GFP for all blanc wells (no virus) and VC was computed as the median GFP for all control wells (no compound).

The method of Harbron (Statistics in Medicine, 2010, DOI:10.1002/sim3916) was used to assess synergy. Using the Loewe definition, two compounds are characterized as being additive, synergistic or antagonistic by:

$$\frac{d_1}{D_{y,1}} + \frac{d_2}{D_{y,2}} \begin{cases} =1, & \text{additivity} \\ <1, & \text{synergy} \\ >1, & \text{antagonism} \end{cases}$$

where $d_1$ and $d_2$ represent the doses of the two compounds that in combination produce an effect y, and $D_{y,1}$ and $D_{y,2}$ represent the doses of the two compounds that produce the same effect, y, when administered as a monotherapy. A 3PL model (3-parameter log-logistic model) was used for the monotherapy dose-response data, where the baseline response was fixed at one.

Following Harbron's approach, the following models were fitted to the data:
"Additive": assuming no interaction between the two compounds
"Uniform": assuming a constant interaction index τ across all dose combinations
"Linear A": assuming the interaction index linearly depends on the log 10 dose of compound A: $z=\tau_1+\tau_2 \log 10(d_A)$
"Separate A": assuming the interaction index τ takes a separate value for each dose of compound A The latter two models were also considered for compound B:
"Linear B": assuming the interaction index linearly τ depends on the log 10 dose of compound B: $\tau=\tau_1+\tau_2 \log 10(d_B)$
"Separate B": assuming the interaction index τ takes a separate value for each dose of compound B The "Separate A" model was selected for all tested combinations based on Akaike's Information Criterion (AIC). The test results for the combinations of Compound A with various Compounds B are reported below.

Combination: Compound A and Pulmocide Compound (N-(2-fluoro-6-methyl phenyl)-6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxamide) as Compound B

TABLE 2 normalized data for Compound A in combination with pulmocide compound (average across 12 replicates).

|  | A = 0 | A = 0.19 | A = 0.57 | A = 1.7 | A = 5.1 | A = 15 | A = 46 | A = 139 | A = 417 | A = 1250 |
|---|---|---|---|---|---|---|---|---|---|---|
| B = 0 | 0.94 | 0.96 | 0.92 | 0.78 | 0.56 | 0.43 | 0.36 | 0.20 | 0.11 | 0.06 |
| B = 0.058 | 0.99 | 0.99 | 0.93 | 0.81 | 0.56 | 0.39 | 0.28 | 0.17 | 0.08 | 0.04 |
| B = 0.17 | 0.99 | 0.99 | 0.91 | 0.74 | 0.51 | 0.37 | 0.23 | 0.16 | 0.08 | 0.04 |
| B = 0.52 | 1.04 | 0.96 | 0.87 | 0.70 | 0.45 | 0.31 | 0.23 | 0.14 | 0.07 | 0.04 |
| B = 1.6 | 0.91 | 0.87 | 0.75 | 0.46 | 0.27 | 0.18 | 0.11 | 0.06 | 0.04 | 0.02 |
| B = 4.7 | 0.20 | 0.14 | 0.12 | 0.06 | 0.03 | 0.01 | 0.01 | −0.00 | −0.00 | −0.00 |
| B = 14 | 0.02 | 0.01 | −0.00 | −0.01 | −0.01 | −0.01 | −0.02 | −0.01 | −0.01 | −0.01 |
| B = 42 | 0.02 | 0.01 | 0.01 | 0.00 | −0.00 | −0.01 | −0.01 | −0.00 | −0.00 | −0.00 |

Table 3 shows the interaction index (τ) estimates with 95% confidence intervals (CIs) for the "separate A" model. Allowing the degree of synergy to vary by doses of Compound A, reveals a significant degree of synergy for doses of 0.57 nM and higher. Overall, the degree of synergy increases with increasing dose levels with a plateau around 5.1 to 139 nM.

TABLE 3 estimated values for interaction indices with 95% CIs for 'separate A' model. The interaction index at the EC50 value is approximated by linear interpolation of the tau estimates.

|  | Dose (nM) | Estimate | 95% CI |
|---|---|---|---|
| $\tau_1$ | 0.19 | 1.013 | (0.955, 1.075) |
| $\tau_2$ | 0.57 | 0.93 | (0.875, 0.989) |
| $\tau_3$ | 1.7 | 0.636 | (0.601, 0.674) |
| $\tau_4$ | 5.1 | 0.479 | (0.449, 0.51) |
| $\tau_5$ | 15 | 0.484 | (0.443, 0.528) |
| $\tau_6$ | 46 | 0.544 | (0.479, 0.618) |
| $\tau_7$ | 139 | 0.51 | (0.412, 0.632) |
| $\tau_8$ | 417 | 0.234 | (0.198, 0.277) |
| $\tau_9$ | 1250 | 0.073 | (0.06, 0.088) |
| τ EC 50 | 9.79 | 0.481 | (NA, NA) |

Combination: Compound A and Palivizumab as Compound B

TABLE 4 normalized data for Compound A in combination with palivizumab as compound B (average across 12 replicates).

|           | A = 0 | A = 0.19 | A = 0.57 | A = 1.7 | A = 5.1 | A = 15 | A = 46 | A = 139 | A = 417 | A = 1250 |
|-----------|-------|----------|----------|---------|---------|--------|--------|---------|---------|----------|
| B = 0     | 1.11  | 1.04     | 0.98     | 0.86    | 0.57    | 0.38   | 0.28   | 0.17    | 0.09    | 0.05     |
| B = 0.0061| 1.05  | 0.99     | 0.93     | 0.77    | 0.51    | 0.34   | 0.26   | 0.15    | 0.08    | 0.04     |
| B = 0.018 | 1.01  | 0.94     | 0.88     | 0.74    | 0.44    | 0.30   | 0.19   | 0.12    | 0.06    | 0.03     |
| B = 0.055 | 0.97  | 0.90     | 0.84     | 0.69    | 0.42    | 0.26   | 0.20   | 0.12    | 0.06    | 0.03     |
| B = 0.165 | 1.01  | 0.93     | 0.82     | 0.64    | 0.32    | 0.16   | 0.11   | 0.06    | 0.03    | 0.02     |
| B = 0.494 | 0.89  | 0.78     | 0.61     | 0.25    | 0.08    | 0.04   | 0.02   | 0.00    | 0.00    | 0.00     |
| B = 1.482 | 0.33  | 0.13     | 0.08     | 0.02    | 0.01    | 0.00   | 0.00   | 0.00    | 0.00    | 0.00     |
| B = 4.447 | 0.06  | 0.03     | 0.02     | 0.01    | 0.01    | 0.00   | 0.00   | 0.00    | 0.00    | 0.00     |

Table 5 shows the interaction index ($\tau$) estimates with 95% confidence intervals (CIs) for the "separate A" model. Note that the model was fitted by fixing the slope in the 3PL model for Compound B at the estimate obtained from the monotherapy fit. Allowing the degree of synergy to vary by doses of Compound A, reveals a significant degree of synergy for all dose levels considered. Overall, the degree of synergy increases with increasing dose levels with a plateau around 5.1 to 139 nM.

TABLE 5 estimated values for interaction indices with 95% CIs for 'separate A' model. The interaction index at the EC50 value is approximated by linear interpolation of the tau estimates.

|            | Dose (nM) | Estimate | 95% CI           |
|------------|-----------|----------|------------------|
| $\tau_1$   | 0.19      | 0.788    | (0.726, 0.855)   |
| $\tau_2$   | 0.57      | 0.626    | (0.579, 0.678)   |
| $\tau_3$   | 1.7       | 0.386    | (0.357, 0.418)   |
| $\tau_4$   | 5.1       | 0.248    | (0.224, 0.273)   |
| $\tau_5$   | 15        | 0.237    | (0.206, 0.273)   |
| $\tau_6$   | 46        | 0.31     | (0.253, 0.38)    |
| $\tau_7$   | 139       | 0.274    | (0.185, 0.407)   |
| $\tau_8$   | 417       | 0.101    | (0.044, 0.232)   |
| $\tau_9$   | 1250      | 0.036    | (0.018, 0.076)   |
| $\tau$ EC 50 | 7.6     | 0.245    | (NA, NA)         |

Combination: Compound A and AZ-27 as Compound B

TABLE 6 normalized data for Compound A in combination with AZ-27 as compound B (average across 12 replicates).

|          | A = 0 | A = 0.19 | A = 0.57 | A = 1.7 | A = 5.1 | A = 15 | A = 46 | A = 139 | A = 417 | A = 1250 |
|----------|-------|----------|----------|---------|---------|--------|--------|---------|---------|----------|
| B = 0    | 0.99  | 0.98     | 0.96     | 0.89    | 0.71    | 0.45   | 0.25   | 0.17    | 0.07    | 0.04     |
| B = 17   | 1.03  | 0.98     | 0.97     | 0.86    | 0.60    | 0.34   | 0.20   | 0.12    | 0.05    | 0.03     |
| B = 51   | 1.00  | 0.93     | 0.90     | 0.72    | 0.45    | 0.23   | 0.13   | 0.07    | 0.03    | 0.02     |
| B = 154  | 0.53  | 0.43     | 0.38     | 0.22    | 0.10    | 0.05   | 0.03   | 0.02    | 0.01    | 0.01     |
| B = 463  | 0.07  | 0.05     | 0.04     | 0.03    | 0.00    | −0.01  | −0.00  | −0.01   | −0.01   | −0.00    |
| B = 1389 | 0.01  | 0.00     | 0.00     | −0.01   | −0.01   | −0.01  | −0.00  | −0.00   | −0.00   | −0.00    |
| B = 4167 | 0.00  | 0.00     | 0.00     | −0.00   | −0.01   | −0.01  | −0.00  | 0.00    | −0.00   | 0.00     |

Table 7 shows the interaction index ($\tau$) estimates with 95% CIs for the "separate A" model. Allowing the degree of synergy to vary by doses of Compound A, reveals a significant degree of synergy for all dose levels considered. Overall, the degree of synergy increases with increasing dose levels with a plateau around 5.1 to 139 nM.

TABLE 7 estimated values for interaction indices with 95% CIs for 'separate A' model. The interaction index at the EC50 value is approximated by linear interpolation of the tau estimates.

|            | Dose (nM) | Estimate | 95% CI           |
|------------|-----------|----------|------------------|
| $\tau_1$   | 0.19      | 0.922    | (0.896, 0.949)   |
| $\tau_2$   | 0.57      | 0.894    | (0.867, 0.923)   |
| $\tau_3$   | 1.7       | 0.755    | (0.724, 0.788)   |
| $\tau_4$   | 5.1       | 0.609    | (0.579, 0.642)   |
| $\tau_5$   | 15        | 0.537    | (0.499, 0.578)   |
| $\tau_6$   | 46        | 0.582    | (0.515, 0.658)   |
| $\tau_7$   | 139       | 0.57     | (0.43, 0.755)    |
| $\tau_8$   | 417       | 0.312    | (0.171, 0.57)    |
| $\tau_9$   | 1250      | 0.126    | (0.093, 0.17)    |
| $\tau$ EC 50 | 11.99   | 0.559    | (NA, NA)         |

Combination: Compound A and GS-5806 as Compound B

TABLE 8 normalized data for Compound A in combination with GS-5806 as compound B (average across 12 replicates).

|          | A = 0 | A = 0.19 | A = 0.57 | A = 1.7 | A = 5.1 | A = 15 | A = 46 | A = 139 | A = 417 | A = 1250 |
|----------|-------|----------|----------|---------|---------|--------|--------|---------|---------|----------|
| B = 0    | 1.06  | 0.99     | 0.93     | 0.83    | 0.47    | 0.30   | 0.21   | 0.11    | 0.06    | 0.03     |
| B = 0.051| 0.99  | 0.96     | 0.91     | 0.71    | 0.44    | 0.23   | 0.17   | 0.09    | 0.05    | 0.03     |
| B = 0.15 | 0.98  | 0.91     | 0.87     | 0.68    | 0.39    | 0.22   | 0.17   | 0.08    | 0.05    | 0.02     |
| B = 0.46 | 0.83  | 0.82     | 0.74     | 0.50    | 0.32    | 0.21   | 0.13   | 0.08    | 0.04    | 0.01     |
| B = 1.4  | 0.36  | 0.39     | 0.27     | 0.21    | 0.18    | 0.17   | 0.13   | 0.08    | 0.04    | 0.01     |
| B = 4.2  | 0.19  | 0.13     | 0.09     | 0.07    | 0.06    | 0.08   | 0.12   | 0.08    | 0.04    | 0.02     |
| B = 12.5 | 0.06  | 0.05     | 0.06     | 0.03    | 0.03    | 0.04   | 0.04   | 0.04    | 0.04    | 0.03     |
| B = 37.5 | 0.05  | 0.03     | 0.03     | 0.03    | 0.03    | 0.02   | 0.02   | 0.03    | 0.04    | 0.03     |

Table 9 show the interaction index ($\tau$) estimates with 95% confidence intervals (CIs) for the "separate A" model. Allowing the degree of synergy to vary by doses of Compound A, reveals a significant degree of synergy for doses of 0.57 to 15 nM. Note that the interaction index at the highest concentration was not estimable.

TABLE 9 estimated values for interaction indices with 95% CIs for 'separate A' model. The interaction index at the EC50 value is approximated by linear interpolation of the tau estimates.

|          | Dose (nM) | Estimate | 95% CI           |
|----------|-----------|----------|------------------|
| $\tau_1$ | 0.19      | 1.063    | (0.985, 1.148)   |
| $\tau_2$ | 0.57      | 0.895    | (0.832, 0.963)   |
| $\tau_3$ | 1.7       | 0.728    | (0.678, 0.78)    |
| $\tau_4$ | 5.1       | 0.678    | (0.621, 0.74)    |
| $\tau_5$ | 15        | 0.783    | (0.684, 0.897)   |
| $\tau_6$ | 46        | 1.321    | (1.091, 1.598)   |
| $\tau_7$ | 139       | 0.938    | (0.469, 1.878)   |
| $\tau_8$ | 417       | 0.037    | (0.007, 0.204)   |
| $\tau_9$ | 1250      | 0        | (NA, NA)         |
| $\tau$ EC 50 | 5.17  | 0.679    | (NA, NA)         |

Combination: Compound A and MDT-637 as Compound B

Note that for the separate A model, the interaction indices at the two highest concentrations were not estimable ($\tau_8$ and $\tau_9$) and the results are based on a local optimum. Table 11 show the interaction index ($\tau$) estimates with 95% confidence intervals (CIs) for the "separate A" model. Allowing the degree of synergy to vary by doses of Compound A, reveals a significant degree of synergy for doses of 0.19 to 15 nM.

TABLE 11 estimated values for interaction indices with 95% CIs for 'separate A' model. The interaction index at the EC50 value is approximated by linear interpolation of the tau estimates.

|          | Dose (nM) | Estimate | 95% CI           |
|----------|-----------|----------|------------------|
| $\tau_1$ | 0.19      | 0.93     | (0.87, 0.995)    |
| $\tau_2$ | 0.57      | 0.865    | (0.811, 0.924)   |
| $\tau_3$ | 1.7       | 0.756    | (0.709, 0.806)   |
| $\tau_4$ | 5.1       | 0.668    | (0.615, 0.726)   |
| $\tau_5$ | 15        | 0.756    | (0.665, 0.859)   |
| $\tau_6$ | 46        | 1.081    | (0.875, 1.334)   |
| $\tau_7$ | 139       | 1.111    | (0.542, 2.278)   |
| $\tau_8$ | 417       | 0.225    | (NA, NA)         |
| $\tau_9$ | 1250      | 0        | (NA, NA)         |
| $\tau$ EC 50 | 4.85  | 0.674    | (NA, NA)         |

TABLE 10 normalized data for Compound A in combination with MDT-637 as compound B (average across 12 replicates).

|          | A = 0 | A = 0.19 | A = 0.57 | A = 1.7 | A = 5.1 | A = 15 | A = 46 | A = 139 | A = 417 | A = 1250 |
|----------|-------|----------|----------|---------|---------|--------|--------|---------|---------|----------|
| B = 0    | 1.01  | 0.98     | 0.97     | 0.85    | 0.43    | 0.26   | 0.16   | 0.06    | 0.02    | −0.00    |
| B = 0.038| 1.01  | 0.98     | 0.90     | 0.76    | 0.41    | 0.22   | 0.11   | 0.04    | 0.01    | −0.01    |
| B = 0.12 | 0.99  | 0.95     | 0.89     | 0.72    | 0.39    | 0.17   | 0.09   | 0.03    | −0.00   | −0.02    |
| B = 0.35 | 0.95  | 0.93     | 0.86     | 0.65    | 0.36    | 0.15   | 0.09   | 0.04    | −0.01   | −0.01    |
| B = 1    | 0.93  | 0.89     | 0.80     | 0.58    | 0.30    | 0.16   | 0.07   | 0.03    | −0.00   | −0.02    |
| B = 3.1  | 0.75  | 0.69     | 0.59     | 0.38    | 0.23    | 0.12   | 0.07   | 0.03    | 0.00    | −0.01    |
| B = 9.3  | 0.14  | 0.11     | 0.10     | 0.10    | 0.11    | 0.11   | 0.08   | 0.04    | 0.00    | −0.01    |
| B = 28   | 0.01  | 0.00     | −0.00    | −0.01   | 0.04    | 0.08   | 0.08   | 0.05    | 0.02    | 0.00     |

Combination: Compound A and 4-amino-8-[3-[[2-(3,4-dimethoxyphenyl)-ethyl]amino]propyl]-6,6-dimethyl-2-(4-methyl-3-nitrophenyl)-3H-imidazo[4,5-h]isoquinoline-7,9(6H,8H)-dione as Compound B

TABLE 12 normalized data for Compound A in combination with 4-amino-8-[3-[[2-(3,4-dimethoxyphenyl)ethyl]amino]propyl]-6,6-dimethyl-2-(4-methyl-3-nitrophenyl)-3H-Imidazo[4,5-h]isoquinoline-7,9(6H,8H)-dione as compound B (average across 12 replicates).

|         | A = 0 | A = 0.19 | A = 0.57 | A = 1.7 | A = 5.1 | A = 15 | A = 46 | A = 139 | A = 417 | A = 1250 |
|---------|-------|----------|----------|---------|---------|--------|--------|---------|---------|----------|
| B = 0   | 1.02  | 0.99     | 0.96     | 0.83    | 0.50    | 0.31   | 0.19   | 0.10    | 0.06    | 0.04     |
| B = 1.9 | 0.99  | 0.96     | 0.89     | 0.74    | 0.47    | 0.24   | 0.16   | 0.09    | 0.05    | 0.01     |
| B = 5.7 | 0.97  | 0.94     | 0.85     | 0.73    | 0.43    | 0.24   | 0.13   | 0.08    | 0.04    | 0.02     |
| B = 17  | 0.89  | 0.84     | 0.79     | 0.64    | 0.35    | 0.20   | 0.15   | 0.05    | 0.04    | 0.01     |
| B = 51  | 0.74  | 0.65     | 0.60     | 0.47    | 0.22    | 0.18   | 0.09   | 0.05    | 0.02    | 0.01     |
| B = 154 | 0.38  | 0.38     | 0.34     | 0.22    | 0.11    | 0.05   | 0.03   | 0.02    | 0.01    | 0.01     |
| B = 463 | 0.05  | 0.03     | 0.04     | 0.03    | 0.01    | 0.01   | 0.01   | −0.00   | −0.00   | −0.00    |
| B = 1389| 0.01  | 0.01     | 0.00     | 0.00    | −0.00   | 0.00   | 0.00   | 0.00    | 0.00    | 0.00     |

Note that there was a manufacturing error at column 1 of the 3rd plate corresponding to monotherapy data for Compound B, and that these data were disregarded in the analysis (resulting in 10 instead of 12 replicates). Table 13 show the interaction index ($\tau$) estimates with 95% confidence intervals (CIs) for the "separate A" model. Allowing the degree of synergy to vary by doses of Compound A, reveals a significant degree of synergy for concentrations of 0.57 to 46 nM.

TABLE 13 estimated values for interaction indices with 95% CIs for 'separate A' model. The interaction index at the EC50 value is approximated by linear interpolation of the tau estimates.

|            | Dose (nM) | Estimate | 95% CI          |
|------------|-----------|----------|-----------------|
| $\tau_1$   | 0.19      | 0.954    | (0.878, 1.037)  |
| $\tau_2$   | 0.57      | 0.89     | (0.821, 0.964)  |
| $\tau_3$   | 1.7       | 0.72     | (0.668, 0.776)  |
| $\tau_4$   | 5.1       | 0.49     | (0.449, 0.534)  |
| $\tau_5$   | 15        | 0.512    | (0.453, 0.579)  |
| $\tau_6$   | 46        | 0.682    | (0.57, 0.816)   |
| $\tau_7$   | 139       | 0.762    | (0.548, 1.061)  |
| $\tau_8$   | 417       | 0.847    | (0.454, 1.583)  |
| $\tau_9$   | 1250      | 0.85     | (0.34, 2.129)   |
| $\tau$ EC 50 | 5.39    | 0.49     | (NA, NA)        |

Combination: Compound a and the Monoclonal Antibody CR9501 as Compound B

Table 15 show the interaction index ($\tau$) estimates with 95% confidence intervals (CIs) for the "separate A" model. Allowing the degree of synergy to vary by doses of Compound A, reveals a significant degree of synergy for all concentrations.

TABLE 15 estimated values for interaction indices with 95% CIs for 'separate A' model. The interaction index at the EC50 value is approximated by linear interpolation of the tau estimates.

|            | Dose (nM) | Estimate | 95% CI          |
|------------|-----------|----------|-----------------|
| $\tau_1$   | 0.19      | 0.844    | (0.772, 0.921)  |
| $\tau_2$   | 0.57      | 0.599    | (0.55, 0.652)   |
| $\tau_3$   | 1.7       | 0.375    | (0.343, 0.41)   |
| $\tau_4$   | 5.1       | 0.21     | (0.187, 0.235)  |
| $\tau_5$   | 15        | 0.217    | (0.186, 0.253)  |
| $\tau_6$   | 46        | 0.245    | (0.195, 0.308)  |
| $\tau_7$   | 139       | 0.243    | (0.161, 0.367)  |
| $\tau_8$   | 417       | 0.059    | (0.009, 0.407)  |
| $\tau_9$   | 1250      | 0.023    | (0.003, 0.176)  |
| $\tau$ EC 50 | 8.93    | 0.212    | (NA, NA)        |

TABLE 14 normalized data for Compound A in combination with CR9501 as compound B (average across 12 replicates).

|            | A = 0 | A = 0.19 | A = 0.57 | A = 1.7 | A = 5.1 | A = 15 | A = 46 | A = 139 | A = 417 | A = 1250 |
|------------|-------|----------|----------|---------|---------|--------|--------|---------|---------|----------|
| B = 0      | 1.06  | 1.05     | 1.01     | 0.89    | 0.64    | 0.41   | 0.28   | 0.21    | 0.10    | 0.06     |
| B = 0.002  | 1.06  | 0.98     | 0.94     | 0.80    | 0.51    | 0.37   | 0.26   | 0.17    | 0.06    | 0.04     |
| B = 0.0061 | 0.99  | 0.94     | 0.89     | 0.73    | 0.43    | 0.30   | 0.21   | 0.13    | 0.05    | 0.04     |
| B = 0.018  | 0.93  | 0.88     | 0.79     | 0.67    | 0.39    | 0.26   | 0.18   | 0.10    | 0.04    | 0.02     |
| B = 0.055  | 0.99  | 0.92     | 0.80     | 0.52    | 0.24    | 0.15   | 0.07   | 0.04    | 0.02    | 0.01     |
| B = 0.164  | 0.77  | 0.66     | 0.49     | 0.26    | 0.07    | 0.03   | 0.01   | 0.00    | 0.00    | 0.00     |
| B = 0.493  | 0.28  | 0.18     | 0.09     | 0.03    | 0.01    | −0.00  | 0.00   | 0.00    | 0.00    | 0.00     |
| B = 1.48   | 0.04  | 0.02     | 0.01     | 0.01    | 0.00    | 0.00   | 0.00   | 0.00    | 0.00    | 0.00     |

Combination: Compound a and Ribavirin as Compound B

TABLE 16 normalized data for Compound A in combination with ribavirin as compound B (average across 12 replicates).

|  | A = 0 | A = 0.19 | A = 0.57 | A = 1.7 | A = 5.1 | A = 15 | A = 46 | A = 139 | A = 417 | A = 1250 |
|---|---|---|---|---|---|---|---|---|---|---|
| B = 0 | 1.01 | 0.97 | 0.95 | 0.87 | 0.63 | 0.39 | 0.25 | 0.15 | 0.08 | 0.04 |
| B = 69 | 1.00 | 0.99 | 0.93 | 0.81 | 0.54 | 0.33 | 0.23 | 0.15 | 0.07 | 0.05 |
| B = 206 | 0.98 | 0.95 | 0.85 | 0.77 | 0.51 | 0.34 | 0.23 | 0.14 | 0.07 | 0.04 |
| B = 617 | 0.98 | 0.88 | 0.86 | 0.72 | 0.49 | 0.29 | 0.20 | 0.13 | 0.06 | 0.04 |
| B = 1852 | 0.97 | 0.91 | 0.83 | 0.69 | 0.46 | 0.22 | 0.16 | 0.11 | 0.05 | 0.03 |
| B = 5556 | 0.94 | 0.91 | 0.83 | 0.63 | 0.34 | 0.16 | 0.13 | 0.07 | 0.04 | 0.03 |
| B = 16667 | 0.83 | 0.72 | 0.62 | 0.39 | 0.17 | 0.08 | 0.06 | 0.04 | 0.03 | 0.02 |
| B = 50000 | 0.13 | 0.12 | 0.09 | 0.05 | 0.02 | 0.01 | 0.02 | 0.02 | 0.01 | 0.01 |

Table 17 show the interaction index ($\tau$) estimates with 95% confidence intervals (CIs) for the "separate A" model. Note that a 2PL model with a lower bound fixed at zero was fitted to the monotherapy data for Compound B. Allowing the degree of synergy to vary by doses of Compound A, reveals a significant degree of synergy for concentrations from 0.19 to 139 nM.

TABLE 17 estimated values for interaction indices with 95% CIs for 'separate A' model. The interaction index at the EC50 value is approximated by linear interpolation of the tau estimates.

|  | Dose (nM) | Estimate | 95% CI |
|---|---|---|---|
| $\tau_1$ | 0.19 | 0.911 | (0.852, 0.974) |
| $\tau_2$ | 0.57 | 0.812 | (0.761, 0.867) |
| $\tau_3$ | 1.7 | 0.61 | (0.572, 0.651) |
| $\tau_4$ | 5.1 | 0.407 | (0.377, 0.44) |
| $\tau_5$ | 15 | 0.338 | (0.303, 0.376) |
| $\tau_6$ | 46 | 0.486 | (0.419, 0.563) |
| $\tau_7$ | 139 | 0.648 | (0.511, 0.822) |
| $\tau_8$ | 417 | 0.652 | (0.378, 1.126) |
| $\tau_9$ | 1250 | 0.934 | (0.347, 2.52) |
| $\tau$ EC 50 | 9.04 | 0.379 | (NA, NA) |

Combination: Compound A and A-60444 as Compound B

TABLE 18 normalized data for Compound A in combination with A-60444 as compound B (average across 12 replicates).

|  | A = 0 | A = 0.19 | A = 0.57 | A = 1.7 | A = 5.1 | A = 15 | A = 46 | A = 139 | A = 417 | A = 1250 |
|---|---|---|---|---|---|---|---|---|---|---|
| B = 0 | 0.97 | 0.96 | 0.95 | 0.83 | 0.55 | 0.38 | 0.28 | 0.14 | 0.07 | 0.04 |
| B = 34 | 1.00 | 0.97 | 0.92 | 0.82 | 0.59 | 0.36 | 0.23 | 0.15 | 0.09 | 0.04 |
| B = 103 | 1.00 | 0.96 | 0.87 | 0.82 | 0.58 | 0.34 | 0.23 | 0.14 | 0.07 | 0.04 |
| B = 309 | 0.96 | 0.93 | 0.88 | 0.75 | 0.52 | 0.30 | 0.22 | 0.16 | 0.07 | 0.04 |
| B = 926 | 0.93 | 0.92 | 0.86 | 0.73 | 0.55 | 0.30 | 0.22 | 0.16 | 0.08 | 0.03 |
| B = 2778 | 0.93 | 0.92 | 0.83 | 0.71 | 0.52 | 0.27 | 0.17 | 0.12 | 0.07 | 0.03 |
| B = 8333 | 0.75 | 0.72 | 0.62 | 0.45 | 0.16 | 0.08 | 0.05 | 0.03 | 0.02 | 0.01 |
| B = 25000 | 0.39 | 0.31 | 0.24 | 0.12 | 0.04 | 0.01 | 0.01 | 0.01 | 0.00 | 0.00 |

Table 19 show the interaction index ($\tau$) estimates with 95% confidence intervals (CIs) for the "separate A" model. Note that a 2PL model with a lower bound fixed at zero was fitted to the monotherapy data for Compound B. Allowing the degree of synergy to vary by doses of Compound A, reveals a significant degree of synergy for concentrations from 0.57 to 139 nM.

TABLE 19 estimated values for interaction indices with 95% CIs for 'separate A' model. The interaction index at the EC50 value is approximated by linear interpolation of the tau estimates.

|  | Dose (nM) | Estimate | 95% CI |
|---|---|---|---|
| $\tau_1$ | 0.19 | 1.072 | (0.976, 1.177) |
| $\tau_2$ | 0.57 | 0.844 | (0.769, 0.926) |
| $\tau_3$ | 1.7 | 0.635 | (0.579, 0.696) |
| $\tau_4$ | 5.1 | 0.407 | (0.368, 0.45) |
| $\tau_5$ | 15 | 0.308 | (0.27, 0.351) |
| $\tau_6$ | 46 | 0.409 | (0.346, 0.484) |
| $\tau_7$ | 139 | 0.631 | (0.502, 0.792) |
| $\tau_8$ | 417 | 0.858 | (0.585, 1.257) |
| $\tau_9$ | 1250 | 1.403 | (0.768, 2.562) |
| $\tau$ EC 50 | 7.89 | 0.379 | (NA, NA) |

The invention claimed is:
1. A combination comprising 3-({5-chloro-1-[3-(methylsulfonyl)propyl]-1H-indol-2-yl-(methyl)-1-(2,2,2-trifluoroethyl)-1.3-dihydro-2H-imidazo[4,5-c]pyridin-2-one, or a pharmaceutically acceptable salt thereof, as Compound A, and one or more Compound B selected from ribavirin, GS-5806, MDT-637, A-60444, AZ-27, CR9501, palivizumab, N-(2-fluoro-6-methylphenyl)-6-(4-(5-methyl-2-(7-oxa-2-azaspiro[3.5]nonan-2-yl)nicotinamido)-benzoyl)-5,6-dihydro-4H-benzo[b]thieno[2,3-d]azepine-2-carboxamide, and 4-amino-8-[3-[[2-(3,4-dimethoxyphenyl)ethyl]amino]

propyl]-6,6-dimethyl-2-(4-methyl-3-nitrophenyl)-3H-imidazo[4,5h]isoquinoline-7,9(6H, 8H)-dione.

2. The combination according to claim 1 wherein Compound B is ribavirin.

3. The combination according to claim 1 wherein Compound B is GS-5806.

4. The combination according to claim 1 wherein Compound B is MDT-637.

5. The combination according to claim 1 wherein Compound B is A-60444.

6. The combination according to claim 1 wherein Compound B is a monoclonal antibody selected from CR9501, and palivizumab.

7. The combination according to claim 1 wherein Compound B is N-(2-fluoro-6-methylphenyl)-6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxamide.

8. The combination according to claim 1 wherein Compound B is 4-amino-8-[3-[[2-(3,4-dimethoxyphenyl)ethyl]amino]propyl]-6,6-dimethyl-2-(4-methyl-3-nitrophenyl)-3H-imidazo[4,5-h]isoquinoline-7,9(6H,8H)-dione.

9. The combination according to claim 1 wherein the amount of Compound A and the amount of Compound B is such that a synergistic antiviral effect against RSV is obtained.

10. The combination according to claim 8 wherein the amount of Compound A ranges from 10 mg to 2500 mg and the amount of Compound B ranges from 10 mg to 2500 mg.

11. A pharmaceutical composition comprising a combination as claimed in claim 1, and a pharmaceutically acceptable carrier.

12. A method for treating or ameliorating RSV infection in a subject in need thereof comprising administering the combination of 3-({5-chloro-1-[3-(methylsulfonyl)propyl]-1 H-indol-2-yl}methyl)-1-(2,2,2-trifluoroethyl)-1,3-dihydro-2H-imidazo[4,5-c]pyridin-2-one, or a pharmaceutically acceptable salt thereof, as Compound A, and one or more Compound B selected from ribavirin, GS-5806, MDT-637, A-60444, AZ-27, CR9501, palivizumab, N-(2-fluoro-6-methylphenyl)-6-(4-(5-methyl-2-(7-oxa-2-azaspiro[3.5]nonan-2-yl)nicotinamido)-benzoyl)-5,6-dihydro-4H-benzo[b]thieno[2,3-d]azepine-2-carboxamide, and 4-amino-8-[3-[[2-(3,4-dimethoxyphenyl)ethyl]amino]propyl]-6,6-dimethyl-2-(4-methyl-3-nitrophenyl)-3H-imidazo[4,5-h]isoquinoline-7,9(6H,8H)-dione.

13. The method as claimed in claim 12 wherein the combination of Compound A and one or more Compound B is formulated in a single pharmaceutical composition.

14. The method as claimed in claim 12 wherein the combination of Compound A and one or more Compound B is formulated as a separate pharmaceutical composition comprising Compound A and a separate pharmaceutical composition comprising one or more Compound B whereby the pharmaceutical compositions are administered simultaneously or sequentially.

\* \* \* \* \*